(12) United States Patent
McLeod

(10) Patent No.: US 9,504,545 B2
(45) Date of Patent: Nov. 29, 2016

(54) DENTAL CONTACT ADJUSTMENT TOOL

(76) Inventor: Neil Stewart McLeod, West Hollywood, CA (US)

(*) Notice: Subject to any disclaimer, the term of this patent is extended or adjusted under 35 U.S.C. 154(b) by 0 days.

(21) Appl. No.: 12/002,375

(22) Filed: Dec. 17, 2007

(65) Prior Publication Data

US 2009/0155739 A1  Jun. 18, 2009

(51) Int. Cl.
*A61C 9/00* (2006.01)
*A61C 19/04* (2006.01)
*A61C 3/00* (2006.01)
*A61C 5/08* (2006.01)

(52) U.S. Cl.
CPC ............ *A61C 19/04* (2013.01); *A61C 3/005* (2013.01); *A61C 5/08* (2013.01)

(58) Field of Classification Search
CPC ...... A61C 11/005; A61C 3/005; A61C 3/10; A61C 19/04; A61C 5/08
USPC ............ 433/50, 70, 75, 141, 3, 68; 401/17, 401/19–21, 28, 221, 57
See application file for complete search history.

(56) References Cited

U.S. PATENT DOCUMENTS

| | | | | |
|---|---|---|---|---|
| 3,719,996 | A * | 3/1973 | Filho | 33/30.2 |
| 4,010,546 | A * | 3/1977 | Ching-Tien | 33/30.1 |
| 4,158,256 | A * | 6/1979 | Wiland et al. | 433/219 |
| 4,992,048 | A * | 2/1991 | Goof | A61C 5/023 433/102 |
| 5,090,127 | A * | 2/1992 | Shapiro et al. | 33/27.02 |
| 5,894,671 | A * | 4/1999 | Karapetian | 33/27.02 |
| 6,125,858 | A * | 10/2000 | Button | 132/321 |
| 7,001,090 | B2 * | 2/2006 | Liu | B43K 5/005 401/56 |
| 7,665,921 | B2 * | 2/2010 | Liu | 401/6 |
| 7,740,479 | B2 * | 6/2010 | Allred et al. | 433/90 |
| 2004/0031114 | A1 * | 2/2004 | Dragan et al. | 15/106 |
| 2004/0076461 | A1 * | 4/2004 | Liu | B43K 21/14 401/17 |
| 2004/0175675 | A1 * | 9/2004 | Brezler et al. | 433/216 |

* cited by examiner

*Primary Examiner* — Cris L Rodriguez
*Assistant Examiner* — Mirayda A Aponte
(74) *Attorney, Agent, or Firm* — William J. Benman; Benman, Brown & Williams

(57) ABSTRACT

A dental contact adjustment tool. The novel dental tool includes a handle and a support structure for coupling a marking apparatus to the handle such that the marking apparatus is at an angle appropriate for delivering a marking medium to an interproximal area of a tooth. In an illustrative embodiment, the support structure includes an angled shaft having a first end coupled to the handle and a second end coupled to a retaining mechanism for holding the marking apparatus at a substantially right angle to the shaft. The marking medium is a transferable medium that will transfer from a tooth to an artificial crown upon contact. In the illustrative embodiment, the marking medium is graphite, and the marking apparatus includes a solid piece of graphite held by a retaining body adapted to interface with the retaining mechanism of the support structure.

12 Claims, 6 Drawing Sheets

DENTAL CONTACT ADJUSTMENT TOOL

BACKGROUND OF THE INVENTION

Field of the Invention

The present invention relates to dental tools. More specifically, the present invention relates to dental tools for fitting artificial crowns.

Description of the Related Art

An artificial dental crown is a typically metal or porcelain device that is placed over a tooth to replace portions of the tooth which have been removed due to decay or damage. Restoring a tooth with a dental crown typically includes several steps: tooth preparation, crown fabrication, and crown fitting and installation. Tooth preparation involves reshaping the tooth (i.e., through filing) so that it is the proper size and shape for receiving a crown. Impressions are then made of the prepared tooth and the adjacent teeth, and teeth above or below the prepared tooth. These impressions are sent to a laboratory which uses them to fabricate the artificial crown. The crown is then fitted and installed during a subsequent visit to the dentist.

During the fitting and installation process, the crown often needs to be adjusted (by grinding and polishing) before it can be permanently affixed to the prepared tooth. The crown may not have a perfect fit due to errors in the fabrication process, or because the patient's teeth may have moved slightly after the impressions for the crown were made. Since it is usually easier and less expensive to correct a crown that is too large than too small, artificial crowns are often intentionally designed to have interproximal contacts (the contacts between the crown and the adjacent teeth) that are slightly tighter than necessary. The tight contacts are then corrected by grinding and polishing until the crown will fit in proper contact with the adjacent teeth.

Fitting the crown typically includes inserting the crown in place over the prepared tooth, observing and/or marking where the crown is too tight, removing the crown, and grinding it with a polishing wheel where needed. These steps are repeated until the crown is the proper size. Determining exactly where the crown needs to be adjusted is often a difficult and uncomfortable process due to the limited space (inside the mouth) within which the dentist has to work, the angle of the teeth, and the lack of tools that can easily mark the locations of the interproximal contacts on the crown. One prior method for marking the interproximal contacts is to insert a thin marking ribbon coated with carbon or dye between the crown and adjacent tooth and removing the ribbon such that a small mark or residue is left on the crown at contact points between the crown and adjacent tooth. These marking ribbons, however, tend to be cumbersome to use and difficult to properly place and remove.

Hence, a need exists in the art for an improved system or method for marking an artificial dental crown that is easier and less cumbersome than prior approaches.

SUMMARY OF THE INVENTION

The need in the art is addressed by the dental contact adjustment tool of the present invention. The novel dental tool includes a handle and a support structure for coupling a marking apparatus to the handle such that the marking apparatus is at an angle appropriate for delivering a marking medium to an interproximal area of a tooth. In an illustrative embodiment, the support structure includes an angled shaft having a first end coupled to the handle and a second end coupled to a retaining mechanism for holding the marking apparatus at a substantially right angle to the shaft. The marking medium is a transferable medium, such that when the medium is applied to a tooth adjacent to a prepared tooth and an artificial crown is inserted in place over the prepared tooth, the medium will transfer from the adjacent tooth to the crown at locations of interproximal contact, leaving visible markings that can be used by the dentist to adjust the fit of the crown. In an illustrative embodiment, the marking medium is graphite, and the marking apparatus includes a solid piece of graphite held by a retaining body adapted to interface with the retaining mechanism of the support structure.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

The present invention provides a novel dental tool for marking an artificial crown for fitting purposes. The novel contact adjustment tool is designed to deliver, at an appropriate angle, a transferable marking medium (such as graphite) to the interproximal contact areas on the adjacent teeth next to the prepared tooth being crowned. When the crown is inserted into place, some of the medium is transferred to the crown at locations where the crown is in contact with the adjacent teeth. Thus, when the crown is removed, it will be marked at the interproximal contact points that need to be adjusted.

Figure 1:
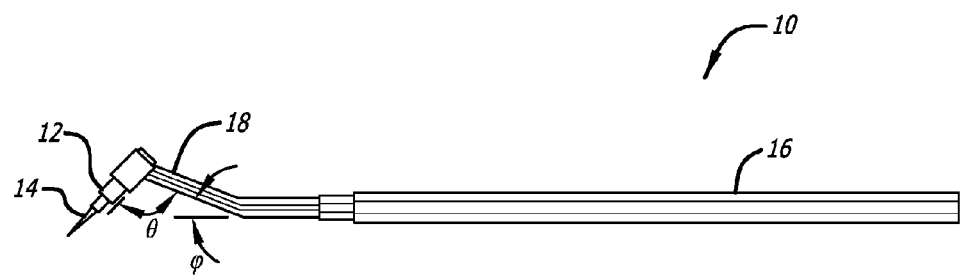
FIG. 1 is a simplified diagram of a contact adjustment tool designed in accordance with an illustrative embodiment of the present invention.

FIG. 1 is a simplified diagram of a contact adjustment tool 10 designed in accordance with an illustrative embodiment of the present invention. The tool 10 includes a marking apparatus 12 for delivering a transferable marking medium 14 to a tooth, a handle 16, and a support structure 18 for connecting the marking apparatus 12 to the handle 16. The support structure 18 is designed to hold the marking apparatus 12 at an appropriate angle such that the medium 14 can be applied to the interproximal area of a tooth, which is the side of the tooth between two adjacent teeth. The marking medium 14 may be any material that can be applied to the tooth that will transfer to the crown upon contact, leaving a visible mark on the crown or vice versa from the artificial crown to the adjacent tooth. In an illustrative embodiment, the marking medium 14 is graphite.

Figure 2:
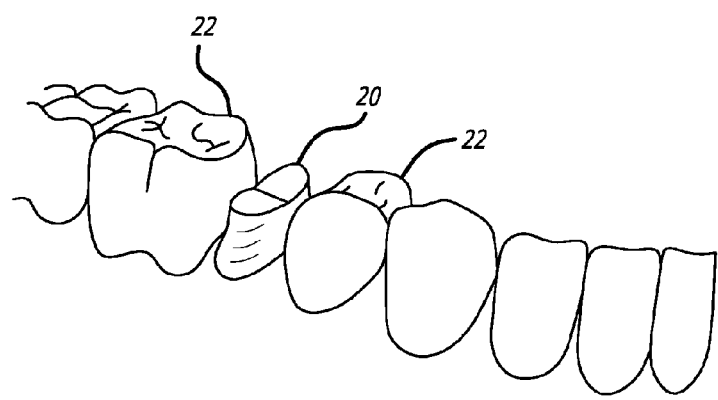
FIG. 2 is an illustration of a prepared tooth that is to be fitted with an artificial crown, and the adjacent teeth next to the prepared tooth.

FIGS. 2-6 show the operation of the illustrative contact adjustment tool 10 in accordance with the present teachings. FIG. 2 is an illustration of a prepared tooth 20 that is to be fitted with an artificial crown, and the adjacent teeth 22 next to the prepared tooth 20. The prepared tooth 20 has been filed down to a size and shape appropriate for receiving a crown.

Figure 3:
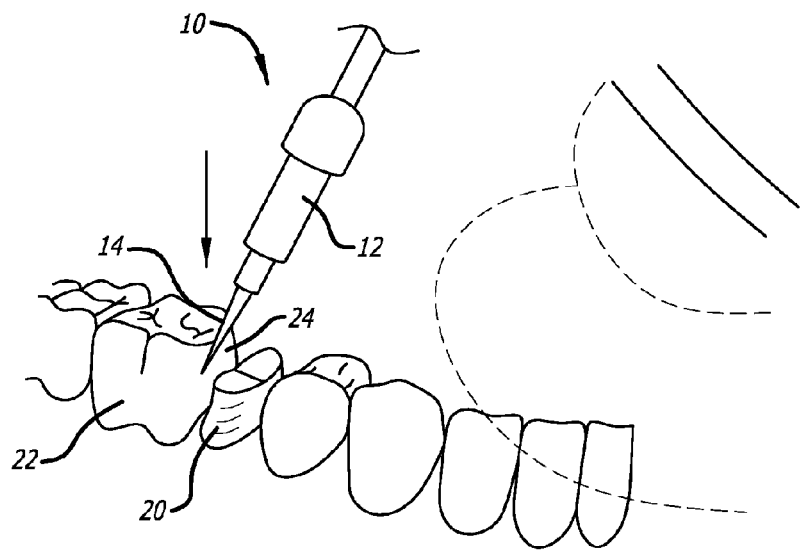
FIG. 3 is an illustration showing the illustrative contact adjustment tool marking the interproximal area of an adjacent tooth in accordance with the present teachings.

FIG. 3 is an illustration showing the illustrative contact adjustment tool 10 marking the interproximal area 24 of an adjacent tooth 22. In the illustrative embodiment, the marking apparatus 12 of the tool 10 includes a piece of graphite 14, similar to pencil lead, which is tapered to allow it to reach down into the narrow space between the adjacent tooth 22 and the prepared tooth 20 (which is typically tapered). The graphite 14 is therefore shaped as a narrow cone. The surface of the graphite cone 14 is rubbed against the interproximal area 24 of the adjacent tooth 22, which is the side of the tooth 22 facing the prepared tooth 20, covering the entire side of the adjacent tooth 22 with a thin layer of graphite.

Figure 4:
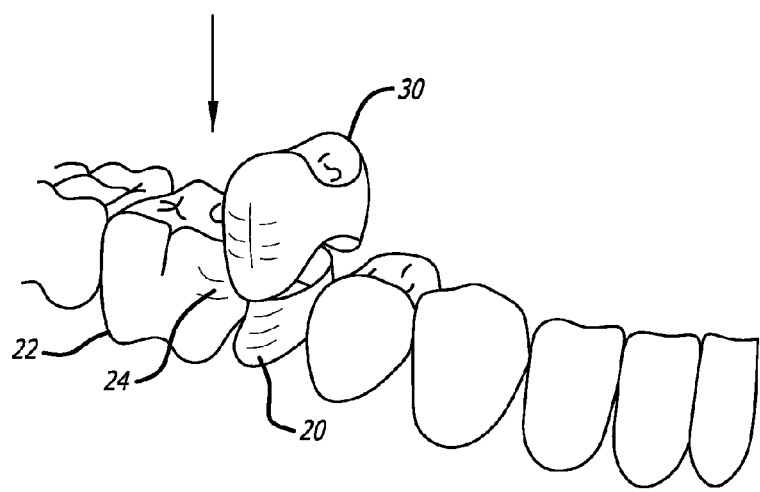
FIG. 4 is an illustration showing an artificial crown being inserted into place over the prepared tooth after the side of the adjacent tooth has been marked by the illustrative contact adjustment tool in accordance with the present teachings.

After the side of the adjacent tooth 22 has been thus marked by the contact adjustment tool 10, the artificial crown is placed over the prepared tooth 20. FIG. 4 is an illustration showing the artificial crown 30 being inserted into place over the prepared tooth 20. If the interproximal contacts of the crown 30 are too tight, they will rub against the graphite marked side 24 of the adjacent tooth 22. The graphite will therefore transfer from the adjacent tooth 22 to the crown 30, leaving a graphite mark at the contact points.

Figure 5:
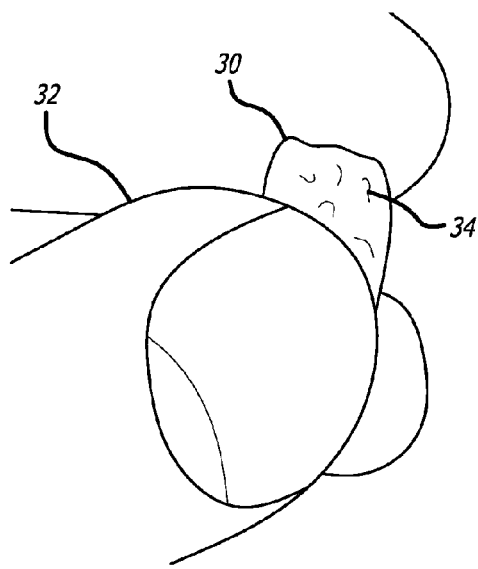
FIG. 5 is an illustration showing the transfer marked crown after it is removed from the prepared tooth.
Figure 6:
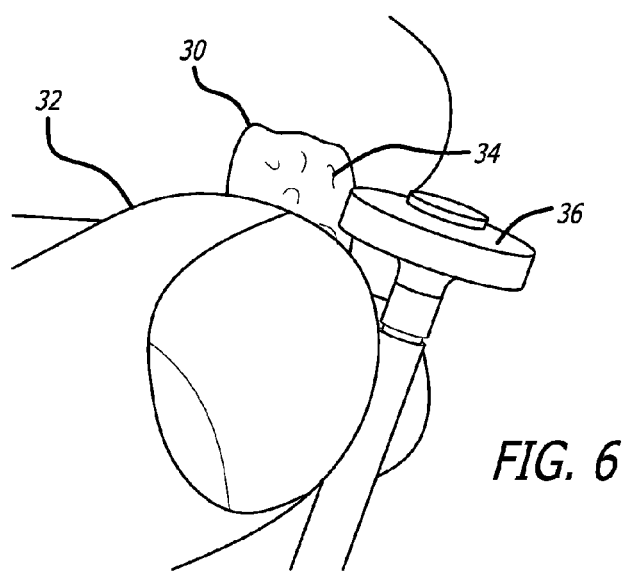
FIG. 6 is an illustration showing the marked crown being adjusted by a polishing wheel at the locations marked with the graphite markings.

The crown 30 is then removed using forceps or a similar tool, or the dentist's fingers 32 as shown in FIG. 5. FIG. 5 is an illustration showing the transfer marked crown 30 after it is removed. The crown 30 is now marked with graphite markings 34 at the interproximal contact points that need to be adjusted. The dentist can then adjust the contact surface with a polishing wheel, correcting the tight contact by reducing it incrementally. FIG. 6 is an illustration showing the marked crown 30 being adjusted by a polishing wheel 36 at the locations marked with the graphite markings 34.

This process of marking and adjusting the crown 30 is repeated as necessary until the crown 30 is the proper size. The crown 30 is then permanently affixed to the prepared tooth 20.

Returning to FIG. 1, the contact adjustment tool 10 of the present invention includes a handle 16, which in the illustrative embodiment is an elongated shaft of an appropriate size such that the handle 16 can be comfortably held and maneuvered by an operator (i.e., the dentist), preferably keeping the operator's hand outside of the patient's mouth.

The support structure 18 couples the marking apparatus 12 to the handle 16. As shown in FIG. 1, the support structure 18 has a smaller average diameter than the handle 16 such that the diameter of the support structure decreases from the handle 16 to the marking apparatus 12. The angle $\theta$ between the support 18 and the marking apparatus 12 is preferably about 90 degrees, allowing the marking apparatus 12 to reach the interproximal contact area, which is the typically very narrow space between adjacent teeth. The support structure 18 itself may also be angled at an angle $\phi$ relative to the handle 16 to provide a more comfortable operational angle for the operator. In the illustrative embodiment of FIG. 1, the support 18 has an angle $\phi$ of about 30 to 40 degrees.

An illustrative technique for using the contact adjustment tool 10 of the present invention is to take hold of the handle 16 between the thumb and index and middle fingers, as if holding a pencil, and to secure a rest with the third finger or the little finger on the crowns of uninvolved teeth in the dental arcade so that inaccurate positioning of the marker 12 is avoided.

The handle 16 and support 18 are preferably made from a rigid material such as metal in order to give the operator greater control over the marking apparatus 12. The handle 16 and support 18 may also be made from other materials, including non-rigid materials, without departing from the scope of the present teachings.

Figure 7:
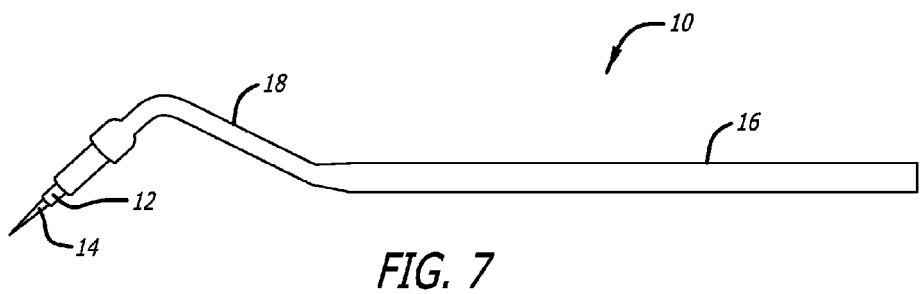
FIG. 7 is a simplified diagram of a contact adjustment tool designed in accordance with an illustrative embodiment of the present invention.

The handle 16 and support structure 18 may be fabricated as a single piece. FIG. 7 is a simplified diagram of a contact adjustment tool 10 designed in accordance with an illustrative embodiment of the present invention, having a handle 16 and support structure 18 as a single piece. The handle 16 and support 18 may also be fabricated as separate pieces (as shown in FIG. 1), and may each be made from a different material. The separate handle 16 and support 18 may be permanently joined (e.g., welded together) or non-permanently joined (such as screwed together).

Figure 8A:
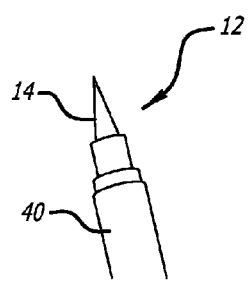
FIG. 8a is a simplified diagram of a removable marking apparatus designed in accordance with an illustrative embodiment of the present invention.

In a preferred embodiment, the marking apparatus 12 is detachable, allowing the marking apparatus 12 to be replaced or sterilized between each use. FIG. 8a is a simplified diagram of a removable marking apparatus 12 designed in accordance with an illustrative embodiment of the present invention. The marking apparatus 12 includes a solid, cone-shaped piece of graphite 14 that is preferably tapered at one end in order to allow a greater reach between teeth. Ideally, the graphite 14 should be able to reach down to where the bottom edge of the crown will be (when in place over the prepared tooth). The other end of the graphite 14 is held by a cylindrical body 40 adapted to interface with the support structure 18. In an illustrative embodiment, the body 40 is made from plastic. The body 40 may also be constructed from other materials without departing from the scope of the present teachings.

Figure 8B:
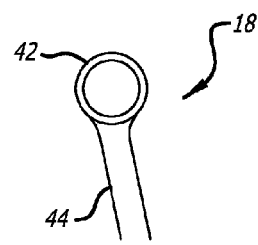
FIG. 8b is a simplified diagram showing a top view of part of a support structure designed in accordance with an illustrative embodiment of the present invention, showing the end of the support that interfaces with the marking apparatus.

FIG. 8*b* is a simplified diagram showing a top view of part of a support structure 18 designed in accordance with an illustrative embodiment of the present invention, showing the end of the support 18 that interfaces with the marking apparatus 12. In this embodiment, the support structure 18 includes a ring retainer 42 within which the marking apparatus 12 is inserted and held in place. The support 18 also includes a shaft 44, which connects the ring 42 to the handle 16. As shown in FIG. 1, the shaft 44 of the support structure 18 may be angled relative to the handle 16 to provide the operator with greater control and maneuverability.

Figure 8C:
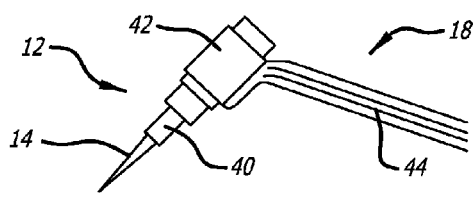
FIG. 8c is a simplified diagram showing a side view of an assembled support structure and marking apparatus designed in accordance with an illustrative embodiment of the present invention.

FIG. 8*c* is a simplified diagram showing a side view of an assembled support structure 18 and marking apparatus 12 designed in accordance with an illustrative embodiment of the present invention. The support structure 18 is designed such that when the marking apparatus 12 is inserted into place in the retaining ring 42, the marking apparatus 12 is approximately at a right angle relative to the support shaft 44, allowing the graphite tip 14 to be maneuvered into the interproximal area between teeth.

Figure 9A:
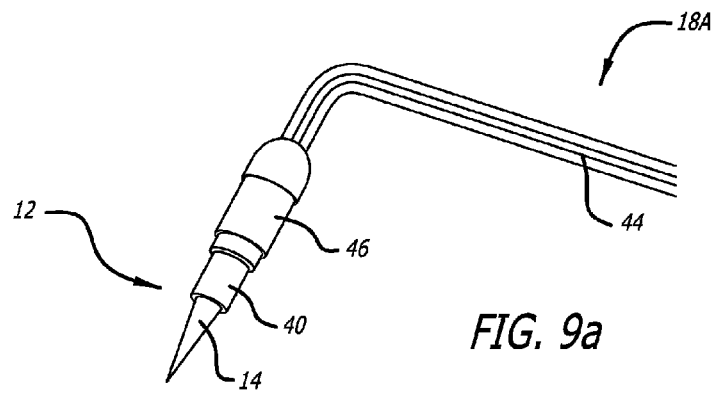
FIG. 9a is a diagram of a support structure with a pressure clip retainer designed in accordance with an illustrative embodiment of the present invention.

FIGS. 9*a*-9*d* show alternative embodiments of the support structure 18, showing different ways the marking apparatus 12 may be coupled to the support structure 18. FIG. 9*a* is a diagram of a support structure 18A with a pressure clip retainer 46 designed in accordance with an illustrative embodiment of the present invention. In this embodiment, the end of the support structure 18A includes a clip retainer 46 adapted to clip onto and hold the marking apparatus 12.

Figure 9B:
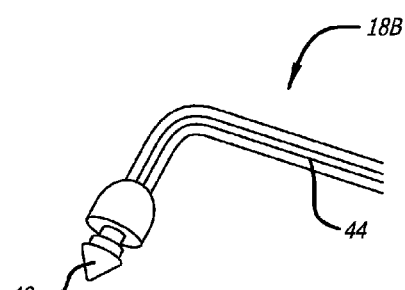
FIG. 9b is a diagram of a support structure with an internal clip retainer designed in accordance with an illustrative embodiment of the present invention.

FIG. 9*b* is a diagram of a support structure 18B with an internal clip retainer 48 designed in accordance with an illustrative embodiment of the present invention. In this embodiment, the cylindrical body 40 of the marking apparatus 12 is hollow, and the end of the support structure 18B includes an internal clip retainer 48 that is designed to be inserted into the hollow end of the marking apparatus 12, thereby holding the marking apparatus 12 in place.

Figure 9C:
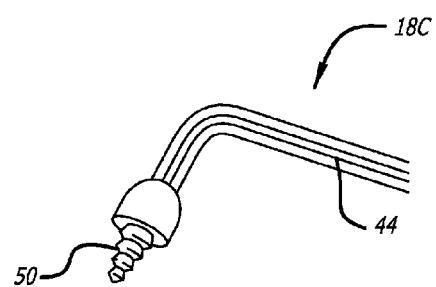
FIG. 9c is a diagram of a support structure with a screw retainer designed in accordance with an illustrative embodiment of the present invention.

FIG. 9*c* is a diagram of a support structure 18C with a screw retainer 50 designed in accordance with an illustrative embodiment of the present invention. In this embodiment, the end of the support structure 18C includes a threaded tip 50 adapted to be screwed into the body 40 of the marking apparatus 12.

Figure 9D:
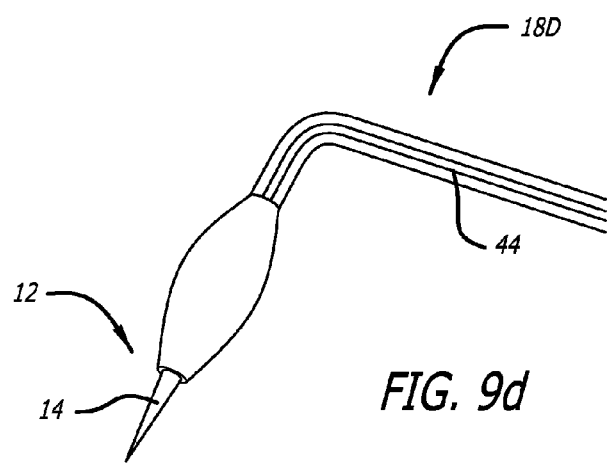
FIG. 9d is a diagram of a welded support structure designed in accordance with an illustrative embodiment of the present invention.

FIG. 9*d* is a diagram of a welded support structure 18D designed in accordance with an illustrative embodiment of the present invention. In this embodiment, the marking apparatus 12, which may include a piece of graphite 14 with or without a retaining body 40, is welded or otherwise permanently affixed to the support structure 18D. For this embodiment, it may be preferable to have a separable support structure 18D and handle 16, so that the support structure 18D and marking apparatus 12 assembly can be replaced between uses.

In the illustrative embodiments described above, the marking apparatus 12 uses a solid piece of graphite 14 as the marking medium. However, the invention is not limited thereto. Other types of marking media and other mechanisms for applying the medium may also be used without departing from the scope of the present teachings.

Figure 10:
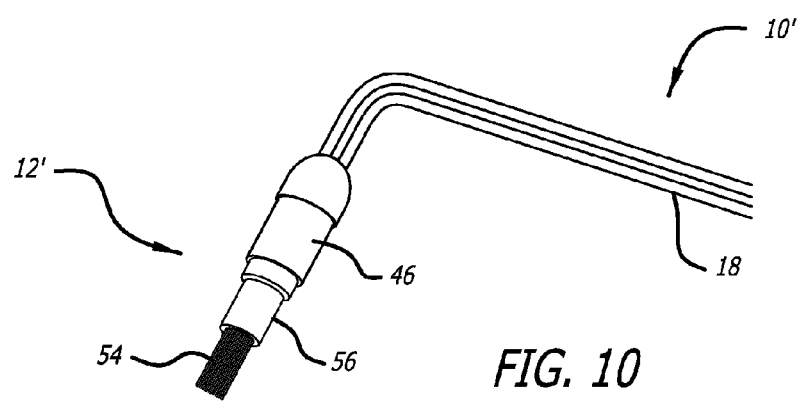
FIG. 10 is a diagram showing part of a contact adjustment tool with a brush tip marking apparatus designed in accordance with an alternate embodiment of the present invention.

For example, FIG. 10 is a diagram showing part of a contact adjustment tool 10' with a brush tip marking apparatus 12' designed in accordance with an alternate embodiment of the present invention. In this embodiment, the transferable marking medium is in a volatile solvent or in a dry powdered form, and the marking apparatus 12' includes a brush or felt tip 54 with which the marking medium is applied to the adjacent tooth surface. The marking apparatus 12' may also include a body 40 that holds the brush or felt tip 54 and is adapted to interface with the support structure 18. As with the previously described embodiments, the marking apparatus 12' may be detachable allowing it to be replaced using a snap pressure clip 46, sleeve ring, screw connector or other mechanism for coupling the marking apparatus 12' to the support structure 18, or it may be part of a complete welded unit.

Thus, the present teachings provide a method for marking an artificial crown that involves applying a layer of graphite or other transferable marking medium onto the interproximal contact area of the adjacent tooth such that when the crown in inserted into place over the prepared tooth, some of the marking medium is transferred to the crown, leaving visible markings at the interproximal contact points. The novel contact adjustment tool described above allows a dentist to apply the marking medium to the interproximal contact area of an adjacent tooth. Alternatively, the transferable medium may be applied to the adjacent tooth using a dental probe, which has an end that is bent at a 90 degree angle. In accordance with the present teachings, the end of the dental probe is coated with a layer of graphite (or other transferable medium). The coated end is then rubbed over the side of the interproximal contact area of an adjacent tooth, transferring some of the graphite from the probe to the tooth. This alternate method, however, may not be as effective at completely covering the side of the tooth with a layer of graphite as compared with the contact adjustment tool described above.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

Accordingly,

What is claimed is:

1. A dental tool consisting of:
   an elongate handle extending through a longitudinal axis;
   a marking medium, said marking medium being a single solid piece of transferrable medium shaped to provide a precise mark on a tooth;
   a detachable marking apparatus for holding and delivering said marking medium to said tooth; and
   a support structure having a first end coupled to said handle and a second end for coupling said marking apparatus to said handle such that said marking apparatus is at an angle appropriate for delivering said marking medium to an interproximal area of said tooth, said support structure having a smaller average diameter than said handle, a first portion thereof coaxial with the longitudinal axis of said handle and a second portion thereof integral with said first portion, said support structure including a retaining ring coaxial with said marking apparatus and adapted to hold said detachable marking apparatus to said second end in response to detachable insertion of said marking apparatus into said retaining ring along said coaxial axis, whereby said second portion is angled at an angle ($\phi$) relative to and away from said longitudinal axis of; said first portion and said handle; said marking apparatus is angled toward said longitudinal axis at an angle ($\theta$) relative to said second portion of said support structure; and said angle ($\phi$) is less than said angle ($\theta$).

2. The dental tool of claim 1 wherein said support structure includes a retaining ring coupled to said marking apparatus and adapted to hold said marking apparatus within said ring.

3. The dental tool of claim 1 wherein said marking medium is transferable from said tooth to an artificial crown upon contact with said crown, or from an artificial crown to a tooth.

4. The dental tool of claim 3 wherein said marking medium is graphite.

5. The dental tool of claim 4 wherein said marking apparatus includes a solid piece of graphite.

6. The dental tool of claim 5 wherein said piece of graphite is tapered.

7. The dental tool of claim 1 wherein said marking medium is tapered at one end in order to allow a greater reach between teeth.

8. The dental tool of claim 7 wherein said marking medium is cone-shaped.

9. The dental tool of claim 7 wherein said marking medium includes a solid piece of graphite.

10. A dental tool consisting of:
an elongate handle extending through a longitudinal axis;
a detachable marking medium;
a marking apparatus for retaining said marking medium; and
a support structure having a first end coupled to said handle and a second end coupled to said marking apparatus, said support structure having a smaller average diameter than said handle such that said tool is tapered from said handle to said marking apparatus, said support structure having a first end coupled to said handle and a second end for coupling said marking apparatus to said handle such that said marking apparatus is at an angle appropriate for delivering said marking medium to an interproximal area of said tooth, said support structure having a first portion thereof coaxial with the longitudinal axis of said handle and a second portion thereof integral with said first portion, said support structure including a retaining ring coaxial with said marking apparatus and adapted to hold said detachable marking apparatus to said second end in response to detachable insertion of said marking apparatus into said retaining ring along said coaxial axis, whereby said second portion is angled at an angle ($\phi$) relative to and away from said longitudinal axis of; said first portion and said handle; said marking apparatus is angled toward said longitudinal axis at an angle ($\theta$) relative to said second portion of said support structure; and said angle ($\phi$) is less than said angle ($\theta$).

11. The invention of claim 10 wherein said handle and said support structure are solid.

12. The invention of claim 11 wherein said handle and said support structure are unitary.

* * * * *